United States Patent [19]

Kuhstoss et al.

[11] Patent Number: 4,766,066
[45] Date of Patent: Aug. 23, 1988

[54] METHOD OF USING BACTERIOPHAGE LAMBDA $P_l$ PROMOTER TO PRODUCE A FUNCTIONAL POLYPEPTIDE IN STREPTOMYCES

[75] Inventors: Stuart A. Kuhstoss; R. Nagaraja Rao, both of Indianapolis, Ind.

[73] Assignee: Eli Lilly and Company, Indianapolis, Ind.

[21] Appl. No.: 655,181

[22] Filed: Sep. 27, 1984

[51] Int. Cl.$^4$ ............... C12P 21/00; C12P 19/34; C12N 15/00; C12N 1/20
[52] U.S. Cl. ............... 435/68; 435/91; 435/172.1; 435/172.3; 435/253; 435/320; 435/886; 435/889; 435/896; 536/27; 935/29; 935/41; 935/43; 935/75
[58] Field of Search ............... 435/68, 70, 71, 91, 435/172.3, 253, 317, 172.1, 320, 886-906; 536/27; 935/29, 41, 43, 75

[56] References Cited

U.S. PATENT DOCUMENTS

| | | | |
|---|---|---|---|
| 4,436,815 | 3/1984 | Hershberger et al. | 435/172.3 |
| 4,460,689 | 7/1984 | Foor et al. | 435/172.3 |
| 4,495,280 | 1/1985 | Bujard et al. | 435/6 |
| 4,506,013 | 3/1985 | Hershberger et al. | 435/172.3 |
| 4,508,826 | 4/1985 | Foor et al. | 435/235 |
| 4,559,300 | 12/1985 | Kovacevic et al. | 435/68 |
| 4,559,302 | 12/1985 | Ingolia | 435/68 |

OTHER PUBLICATIONS

Schottel, J. et al., 1981, J. Bacteriol. 146:360–368.
Remaut, E. et al., 1981, Gene 15:81–93.
Bernard, H. et al., 1979, Methods in Enzymology 68:482–492.
Bernard, H. et al., 1979, Gene 5:59–76.
Hedgpeth, J. et al., 1978, Molec. Gen. Genet. 163:197–203.
Derom. C. et al., 1982, Gene 17:45–54.
Gatenby, A. et al., 1982, Mol. Gen. Genet. 185:424–429.

Primary Examiner—James Martinell
Attorney, Agent, or Firm—Gerald V. Dahling; Leroy Whitaker

[57] ABSTRACT

The invention relates to a method and cloning vehicle for the expression of a functional polypeptide in Streptomyces. A recombinant DNA cloning vehicle was genetically engineered to bring the expression of the neomycin phosphotransferase gene under the control of the *Escherichia coli* bacteriophage $\lambda p_L$ promoter.

17 Claims, 4 Drawing Sheets

Restriction Site and Function Map of Plasmid pKC309
(6821 bp)

METHOD OF USING BACTERIOPHAGE LAMBDA P$_l$ PROMOTER TO PRODUCE A FUNCTIONAL POLYPEPTIDE IN STREPTOMYCES

The present invention is a method of using bacteriophage lambda p$_L$ promoter to produce a functional polypeptide in Streptomyces. A Streptomyces host cell is transformed with a selectable and autonomously replicating recombinant DNA expression vector comprising (1) the bacteriophage lambda p$_L$ promoter-operator transcriptional activating sequence, (2) a translational activating sequence, and (3) a DNA sequence that codes for a functional polypeptide. The above-described expression vector is engineered to generate, upon transcription, a translatable mRNA transcript. The invention further comprises the transformants which are required to employ the aforementioned method.

The present invention provides a method for expressing functional polypeptides in Streptomyces host cells by means of recombinant DNA technology. Heretofore, the development and exploitation of recombinant DNA techniques in the above organisms has been retarded and time-consuming because of the general lack of characterized Streptomyces promoters. On the other hand, a number of *Escherichia coli* promoters have been well characterized. For example, the bacteriophage lambda p$_L$ promoter (λ leftward promoter) is a strong, well-regulated promoter that has been commonly employed in several expression vectors. Initiation of transcription at the λp$_L$ promoter is known to be repressed by the product of the phage gene cI to levels below detection limits. Mutants of the cI gene are available that code for a temperature-sensitive repressor (Lieb, M., 1966, J. Mol. Biol. 16:149) so that transcription from p$_L$ is repressed at low temperature and can be initiated at high temperature. Thus, the promoter has the distinct advantage of being controllable in *E. coli*, a characteristic which is highly desirable where large-scale microbial fermentation production is concerned. The λp$_L$ promoter can also be controlled in Streptomyces provided the λcI gene is present and is designed to be expressed in Streptomyces on either the same plasmid vector as the λp$_L$ promoter, or on an independent vector, or by means of chromosomal integration. Similarly, it is possible to control λp$_L$ expression in Streptomyces using λcro gene product (Cro repressor).

The general paucity of knowledge concerning Streptomyces transcription and translation signals necessitates the development of alternate signals that are functional in Streptomyces. Accordingly, the λp$_L$ promoter transcriptional activating sequence was employed to direct the expression of virtually any polypeptide in Streptomyces. This method for expressing polypeptides in Streptomyces represents a significant advance in the technical art and greatly expands the application of recombinant DNA technology in gram positive microorganisms.

Gene cloning and expression of products in Streptomyces are highly advantageous since the organisms are substantially non-pathogenic and ordinarily do not produce endotoxins. In addition, Streptomyces have been extensively studied and are well known and understood in the antibiotic and fermentation industries. The present method and associated expression vectors and transformants are particularly important because they allow for the commercial exploitation of these important advantages.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Recombinant DNA Expression Vector—any recombinant DNA cloning vector into which one or more transcriptional and translational activator sequence(s) have been incorporated.

Transcriptional Activating Sequence—any DNA sequence that directs or provides for the transcription of DNA into a mRNA transcript.

Translational Activating Sequence—any DNA sequence that provides for the translation of a mRNA transcript into a peptide or polypeptide.

Functional Polypeptide—a recoverable bioactive heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bio-inactivating polypeptide which can be specifically cleaved.

Restriction Fragment—any linear DNA sequence generated by the action of one or more restriction enzymes.

Sensitive Host Cell—a host cell that cannot grow in the presence of a given antibiotic without a DNA segment that confers resistance thereto.

Transformation—the introduction of DNA into a recipient host cell that changes the genotype and consequently results in a change in the recipient cell.

Transformant—a recipient host cell that has undergone transformation.

*Escherichia coli* Origin of Replication—a DNA sequence that controls and allows for replication of a plasmid or other vector in *E. coli*.

Streptomyces Origin of Replication—a DNA sequence that controls and allows for replication of a plasmid or other vector in Streptomyces.

DETAILED DESCRIPTION OF THE INVENTION

Figure 1:
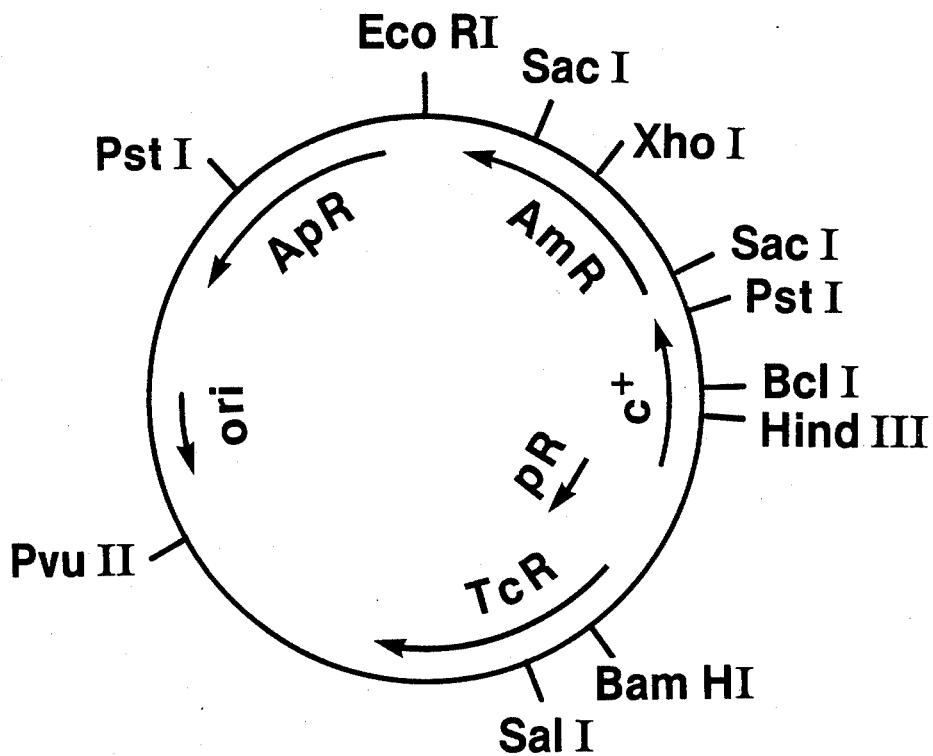
FIG. 1 is a restriction site and function map of plasmid pKC309.

The present invention is a method of using bacteriophage lambda p$_L$ promoter to produce a functional polypeptide in Streptomyces, said method comprising:
  a. transforming a Streptomyces host cell with a selectable and autonomously replicating recombinant DNA expression vector comprising:
    1. the bacteriophage λp$_L$ promoter-operator transcriptional activating sequence;
    2. a translational activating sequence;
    3. a DNA sequence that codes for a functional polypeptide; and
  b. culturing said transformed cell under conditions suitable for expression of said polypeptide, subject to the limitation that said expression vector sequentially contains said $\lambda p_L$ promoter-operator transcriptional activating sequence, said translational activating sequence and said DNA sequence that codes for a functional polypeptide such that a translatable mRNA transcript encodes the functional polypeptide.

The $\lambda p_L$ promoter can either be obtained through a commercial supplier such as P-L Biochemicals, Inc., 1037 West McKinley Ave., Milwaukee, Wis. 53205 or obtained by enzymatic digestion of plasmid pKC283. The fragment isolated from plasmid pKC283 is an $\sim 137$ basepair (bp) BglII restriction fragment containing the $\lambda p_L$ promoter. Plasmid pKC283 is $\sim 9$ kilobases (kb) and can be conventionally isolated from *Escherichia coli* K12 BE1201/pKC283, a strain deposited and made part of the permanent stock culture collection of the Northern Regional Research Laboratory, Peoria, Ill. 61604. The strain is available to the public as a preferred source and stock reservoir of plasmid pKC283 under the accession number NRRL B-15830. *E. coli* K12 BE1201/pKC283 may carry two different plasmids that can be conventionally isolated and separated on the basis of size and the pattern of restriction sites.

The translational activating sequence can be conventionally synthesized by the modified phosphotriester method, using fully protected deoxyribonucleotide building blocks, in substantial accordance with the procedures of Itakura et al., 1977, Science 198:1056 and Crea et al., 1978, Proc. Nat. Acad. Sci. USA 75:5765. Alternatively, the DNA sequence coding for a functional polypeptide may contain a homologous translational activating sequence such as that embodied in the neomycin phosphotransferase gene contained in plasmid pKC356.

The construction of plasmid pKC417 was engineered to bring the expression of the neomycin phosphotransferase gene under the control of the $\lambda p_L$ promoter. Plasmid pKC417 was therefore constructed by inserting the $\sim 137$ bp BglII $\lambda p_L$ promoter-containing restriction fragment into the unique BglII restriction site of plasmid pKC356. The unique BglII restriction site is located directly upstream from the promoterless neomycin phosphotransferase gene in plasmid pKC356. Thus, the ligation of the $\lambda p_L$ promoter to the promoterless neomycin phosphotransferase gene generates a fully operable transcriptional and translational coding sequence for the expression of a functional polypeptide.

The present method for expressing a functional polypeptide in Streptomyces represents a significant technical advance. The aforedescribed $\lambda p_L$ promoter DNA sequence can be used for the universal expression in Streptomyces of any polypeptide-encoding gene. While the specific embodiment of the invention is shown and described, many variations are possible. For example, the present invention is in no way limited to the use of a particular gene encoding a polypeptide since the choice of a specific sequence is not critical to the operability of the present invention. Genes coding for a functional polypeptide can be substituted for the neomycin phosphotransferase coding sequence exemplified above. Such coding sequences include, but are not limited to, sequences that code for human growth hormone, human pregrowth hormone, porcine growth hormone, mammalian growth hormone, avian growth hormone, growth hormone releasing factor, human insulin A chain, human insulin B chain, human proinsulin, human pre-proinsulin, human and non-human interferon, viral antigen, urokinase, tissue plasminogen activator, interleukin II, any peptide hormone, any enzyme or virtually any other polypeptide with research or commercial value.

For convenience and ease of construction, plasmid pKC417 was constructed from a series of starting materials and intermediates exemplified as follows. An $\sim 2.9$ kb BamHI origin of replication-containing fragment of Streptomyces plasmid pEL103 was inserted into BclI-digested pKC309 to generate a bifunctional vector designated as pKC326. Plasmid pEL103, which is used as a starting material for the construction of plasmid pKC326, can be conventionally isolated from *Streptomyces granuloruber* No. A39912.13/pEL103. Plasmid pKC309 is $\sim 7$ kb and contains the ampicillin and apramycin resistance genes as well as an origin of replication that is functional in *E. coli*. Plasmid pKC309 can also be conveniently isolated from *Escherichia coli* K12 BE1041/pKC309. Both the above strains are deposited and made part of the permanent stock culture collection of the Northern Research Laboratory, Peoria, Ill. 61604. The strains are available to the public as a preferred source and stock reservoir of plasmids pEL103 and pKC309 under the respective accession numbers NRRL 12549 and NRRL B-15827.

The resultant vector, pKC326 was subsequently digested with BamHI restriction enzyme and ligated to the thiostrepton resistance-containing BclI fragment of plasmid pIJ702 to form the plasmid pKC345. Plasmid pIJ702, which is used as a starting material for constructing plasmid pKC345, is $\sim 5.6$ kb and can be conventionally isolated from *Streptomyces lividans*/pIJ702, a strain deposited and made part of the permanent stock culture collection of the American Type Culture Collection, 12301 Parklawn Drive, Rockville, Md. 20852. The strain is available to the public as a preferred source and stock reservoir of the plasmid under the accession number ATCC 39155.

Plasmid pKC354 is constructed by ligating the $\sim 2.1$ kb AvaI restriction fragment of plasmid pKC322 to SacI-digested, plasmid pKC345. Both of the fragments were made blunt-ended by treatment with T4 DNA polymerase prior to the ligation step. This resultant bifunctional vector contains an apramycin resistance gene functional in both *Escherichia coli* and Streptomyces and a thiostrepton resistance gene that is functional in Streptomyces, as well as a promoterless hygromycin and promoterless neomycin resistance gene. Plasmid pKC322, which is used as a starting material for constructing plasmid pKC354, can be conventionally isolated from *E. coli*/pKC322, a strain deposited and made part of the permanent stock culture collection of the Northern Regional Research Laboratory. The strain is available as a preferred source and stock reservoir of the plasmid under the accession number NRRL B-15829.

The derivative plasmid pKC356 was constructed by deleting an $\sim 1.5$ kb EcoRI restriction fragment from plasmid pKC354. This EcoRI deletion suceeded in removing substantially all of the hygromycin gene. Plasmid pKC356 is useful in constructing the vectors of the present invention because it is functional in both *Escherichia coli* and Streptomyces, contains drug resistance markers that are functional in either host and contains a promoterless neomycin phosphotransferase gene which is located directly downstream from two unique restriction sites that are available for the insertion of the $\lambda p_L$ promoter transcriptional activating sequence.

Figure 4:
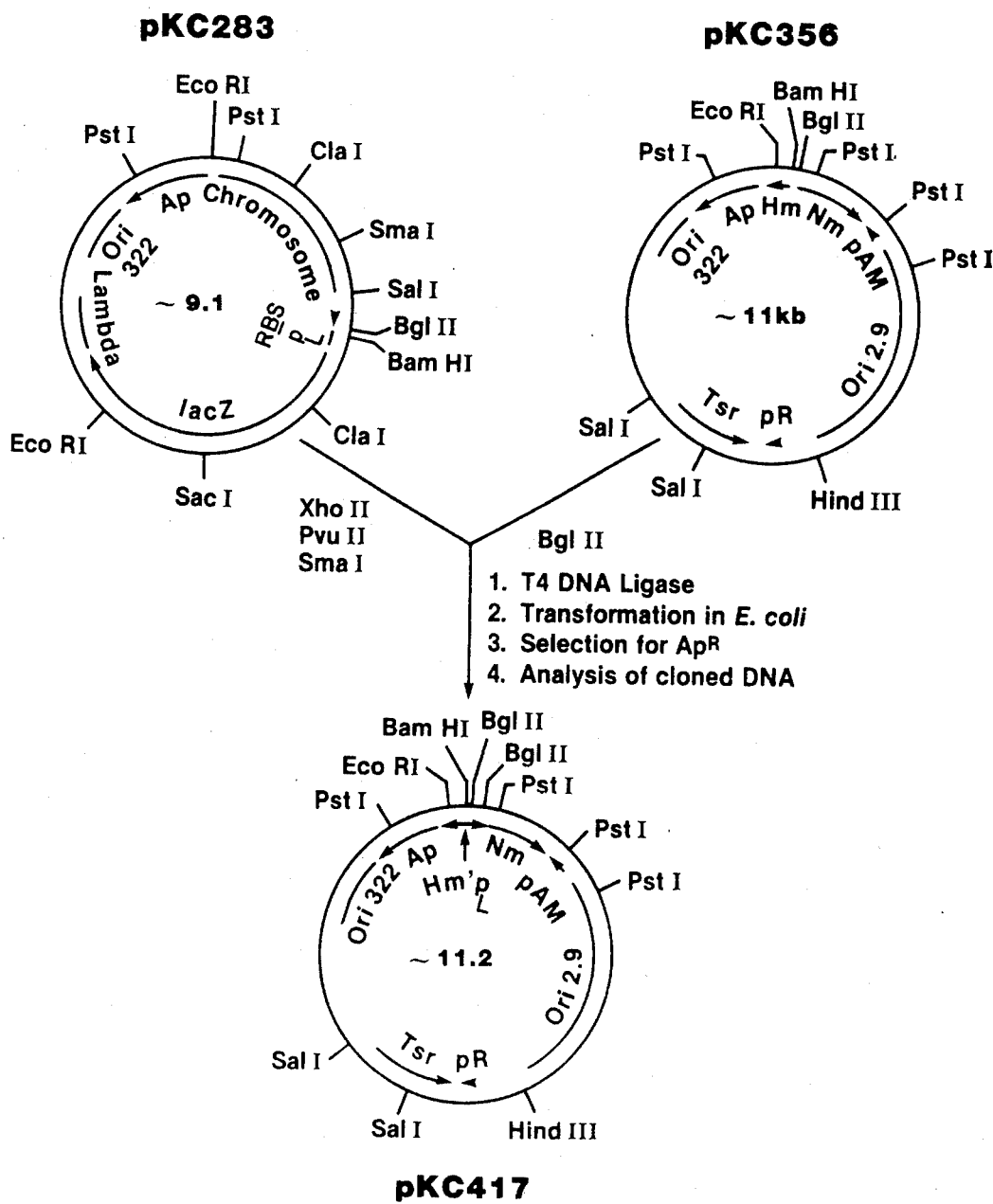
FIG. 4 illustrates the construction of pKC417.

Plasmid pKC417 was constructed to illustrate the expression in Streptomyces of a heterologous gene product which is under the control of a foreign *Escherichia coli* promoter. Accordingly, the aforedescribed ~137 bp BglII restriction fragment of plasmid pKC283 was ligated to BglII-digested plasmid pKC356 resulting in plasmid pKC417. Plasmid pKC417 is functional in both *E. coli* and Streptomyces and comprises a $\lambda p_L$ promoter transcriptional activating sequence, a neomycin phosphotransferase gene containing a homologous ribosome binding site, and a translational activating sequence. Plasmid pKC417 expresses a gene product conferring neomycin resistance in Streptomyces and therefore is useful for exemplifying the present invention. Additionally, the neomycin resistance gene can be used as a selectable marker, thus making the vector generally useful as a molecular cloning vehicle. A restriction site and function map of plasmid pKC417 is presented in FIG. 4 of the accompanying drawings.

The present method for expressing a functional polypeptide in Streptomyces is not limited to a single species or strain of Streptomyces. To the contrary, the present invention is broadly applicable and can be applied to host cells of many Streptomyces taxa, particularly the restrictionless strains thereof. Restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade DNA upon transformation. For purposes of the present application, host cells containing restriction enzymes that do not cut any of the restriction sites of the vectors that are useful for illustrating the present invention are also considered restrictionless.

Preferred host cells of restrictionless strains of Streptomyces taxa that produce aminoglycoside antibiotics and in which the present method can be applied and is especially useful, include restrictionless cells of, for example: *Streptomyces chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin) *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present method can be applied and is especially useful, include restrictionless cells of, for example: *Streptomyces caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetylleukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present method can be applied and is especially useful, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present method can be applied and is especially useful, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present method can be applied and is especially useful, include restrictionless cells of, for example: *Streptomyces orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present method can be applied and is especially useful, include restrictionless cells of, for example: *Streptomyces coelicolor, S. granuloruber, S. roseosporus, S. lividans,* and *S. espinosus.*

While all of the embodiments of the present invention are useful, some of the expression vectors and transformants are preferred for applying the present invention. Accordingly, a preferred vector is plasmid pKC417 and a preferred transformant is *Streptomyces ambofaciens*/pKC417.

The method for expressing functional polypeptides of the present invention has broad utility and helps fill the need for expression vehicles for use in Streptomyces. Thus, the present method allows for the genetic expression in Streptomyces of products now produced in *Escherichia coli*. This is especially advantageous because large scale fermentation of Streptomyces is better known and understood than is fermentation of *E. coli*. In fact, commercial fermentation of *E. coli* is still highly experimental and fraught with difficulty. The present invention circumvents this problem by providing the alternative of producing compounds now synthesized in *E. coli* such as, for example, human insulin, human proinsulin, glucagon, interferon, human growth hormone, bovine growth hormone and the like, in Streptomyces. This can be done because the vectors useful in the present method are highly versatile and can accommodate DNA sequences which encode the aforementioned products. The present method thus allows for flexibility in the choice of hosts and provides a means for using Streptomyces in the production of polypeptides and other gene products. Therefore the use of the $\lambda p_L$ promoter transcriptional activating sequence for the genetic expression of functional polypeptides in Streptomyces allows for the full exploitation of recombinant DNA technology in that industrially important class of microorganisms.

*Streptomyces granuloruber* No. A39912.13/pEL103, *Streptomyces lividans*/pIJ702, *Escherichia coli* K12 BE1041/pKC309, *E. coli* K12 BE1295/pKC322 and *E. coli* K12 BE1201/pKC283, as respective sources of plasmids pEL103, pIJ702, pKC309, pKC322 and pKC283, and *Streptomyces ambofaciens* can be cultured in a number of ways using any of several different media. Carbohydrate sources which are preferred in a culture medium include, for example, molasses, glucose, dextrin, and glycerol, and nitrogen sources include, for example, soy flour, amino acid mixtures and peptones. Nutrient inorganic salts are also incorporated and include the customary salts capable of yielding magnesium, sodium, potassium, ammonium, calcium, phosphate chloride, sulfate, and like ions. As is necessary for the growth and development of other microorganisms, essential trace elements are also added. Such trace elements are commonly supplied as impurities incidental to the addition of other constituents of the medium.

*Streptomyces granuloruber* No. A39912.13/pEL103 and *Streptomyces lividans*/pIJ702 are each grown under aerobic culture conditions over a relatively wide pH range of about 5 to 9 at temperatures ranging from about 15° to 40° C. For production of plasmids pEL103 and pIJ702 in the greatest quantity, however, it is desirable to start with a culture medium of a pH of about 7.2 and maintain a culture temperature of about 30° C. Culturing the Streptomyces cells, under the aformentioned conditions, results in a reservoir of cells from which the plasmids are respectively isolated by techniques well known in the art.

*Escherichia coli* K12 BE1041/pKC309, *E. coli* K12 BE1295/pKC322, and *E. coli* K12 BE1201/pKC283 are each grown under aerobic culture conditions over a relatively wide pH range of about 6.5 to 8 at temperatures ranging from about 25° to 40° C. For production of plasmids pKC309, pKC322 and pKC283 in the greatest quantity, however, it is desirable to start with a culture medium at a pH of about 7.4 and maintain a culture temperature of about 30° C. Culturing the *E. coli* cells, under the aforementioned conditions, results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Culture of *E. coli* K12 BE1281/pKC309 and Isolation of Plasmid pKC309

A. Culture

About 5 ml. cultures of *E. coli* K12 BE1041/pKC309 (NRRL B-15827) were grown under selective conditions in TY media (1% tryptone, 0.5% yeast extract, 0.5% sodium chloride, pH 7.4) according to conventional microbiological procedures. The cells were spun in a table top centrifuge and the pellet resuspended in 1 ml. of 0.3M sucrose, 25 mM EDTA (ethylene diaminetetracetate) and 25 mM Tris-HCl pH 8 (Solution I). After transfer to an Eppendorf tube the cells were centrifuged for about one minute and the pellet was resuspended in 0.5 ml. of Solution I. About 50 μl. of freshly made lysozyme (20 mg./ml. in water) was added and the solution was incubated for 10 minutes at 37° C.

After the addition of 250 μl. of freshly made lysis mix (2% sodium dodecyl sulfate and 0.3N NaOH), the cells were immediately and completely vortexed. The cells were then incubated for ten minutes at 70° C., cooled and added to 100 μl. of phenol-Sevag (phenol-chloroform-isoamyl alcohol, 25-24-1). The material was completely mixed by vortexing. After the DNA was centrifuged for two minutes in an Eppendorf centrifuge the supernatant was decanted and transferred to another tube with 70 μl. of unbuffered 3M sodium acetate and 500 μl. of isopropanol to precipitate the DNA. This solution was incubated for five minutes at room temperature and then centrifuged for five minutes. The supernatant was gently and completely decanted to remove all the excess liquid.

The DNA precipitate was redissolved in 500 μl. of TE (10 mM Tris-HCl pH 8 and 1 mM EDTA) and 25 μl. of 100 mM spermine HCl was added. This mixture was vortexed and then incubated for five minutes at room temperature before a five minute spin in an Eppendorf centrifuge. The supernatant was again completely decanted and discarded and the DNA pellet was washed with 1 ml. of 75% ethanol, 0.3M sodium acetate, and 10 mM magnesium acetate. This solution was incubated for five minutes at room temperature and the DNA collected as above. The pellet was redissolved in 10 μl. of TE for subsequent use as a cloning vehicle.

EXAMPLE 2

Construction of Plasmid pKC345

A. BclI Digestion of Plasmid pKC309

About 10 µl. of plasmid pKC309 DNA (prepared in Example 1) was digested in 1X BclI buffer (75 mM KCl, 10 mM Tris pH 7.4, 10 mM $MgCl_2$, and 10 mM DTT) in a total volume of 50 µl. with 20 units (New England Biolab) of BclI restriction endonuclease*. The mixture was incubated at 50° C. for about 1½ hours. Next, 0.1 volume of 3M sodium acetate (NaOAc) was added which was followed by 3 volumes of 95% ethanol to precipitate the DNA. This ethanol precipitation was rapidly performed in a dry ice-isopropanol bath. The above procedure for an ethanol precipitation was performed throughout the following experiments unless otherwise indicated. The DNA precipitate was collected by centrifugation in an Eppendorf microfuge for 5 minutes. The DNA pellet was washed with ethanol and then vacuum dried and suspended in about 10 µl. of water for subsequent ligation.

*Restriction enzymes and instructions can be obtained from the following sources: New England Bio Labs. Inc., 32 Tozer Road, Beverly, Mass. 01915; Bethesda Research Laboratories, Inc., P.O. Box 577, Gaithersburg, Md. 20760; Boehringer-Mannheim Biochemicals, 7941 Castleway Drive, P.O. Box 50816, Indianapolis, Ind. 46250.

B. Isolation of Plasmid pEL103

1. Culture of *Streptomyces granuloruber* No. A39912.13/pEL103

A vegetative inoculum of *Streptomyces granuloruber* No. A39912.13/pEL103 (NRRL 12549) is conventionally prepared by growing the strain under submerged aerobic conditions in 50 ml. of sterilized trypticase soy broth* at 35 g./l. in deionized water.

The trypticase soy broth inoculum is incubated for 48 hours at a temperature of 30° C. After incubation, about 10 ml. of the inoculum is transferred to 500 ml. of the sterilized broth and incubated for about 20 hours at 30° C. The pH is not adjusted. After incubation, the *Streptomyces granuloruber* No. A39912.13/pEL103 cells are ready for harvest and subsequent isolation of plasmid DNA.

*Trypticase soy broth is obtained from BBL Division, Becton-Dickinson & Company, Cockeysville, Md. 21030

2. Plasmid Isolation

About 12 g. (wet wgt) of *Streptomyces granuloruber* No. A39912.13/pEL103 cells are centrifuged (10 minutes, 4° C., 10,000 rpm), washed in 10% glycerol, and then harvested by recentrifugation under the aforementioned conditions. About 50 ml. of TES buffer (0.01M Tris(hydroxymethyl)aminoethane [Tris], 0.001M EDTA, 34% sucrose, pH 8) are added to the cells followed by about 0.25 g. of lysozyme in 10 ml. of 0.25M EDTA. After the mixture is incubated at 37° C. for about 15 minutes, about 0.5 ml. of 10% Triton X-100 in TE buffer (0.01M Tris, 0.001M EDTA, pH 8) is added. The resultant mixture is then incubated at 65° C. for about 15 minutes. After the lysate is centrifuged (45 minutes, 4° C., 18,000 rpm), the supernatant is extracted four times with isoamyl alcohol and once with a chloroform isoamyl alcohol solution (24:1). Next, 0.1 volume of 3M sodium acetate is added to the aqueous phase followed by 3 volumes of cold (−20° C.) 95% ethanol. The ethanol precipitation is rapidly performed in a dry ice ethanol bath and the DNA precipitate collected by centrifugation (15 minutes, 4° C., 10,000 rpm). The precipitate is vacuum dried and then resuspended in 1.1 ml. of STE buffer (0.01M Tris, 0.001M EDTA, 0.01M sodium chloride). Centrifugation (40 hours, 15° C., 35,000 rpm) using cesium chloride gradients with ethidium bromide, is carried out to purify the plasmid DNA. Following centrifugation, the desired plasmid pEL103 DNA band is removed and the ethidium bromide extracted by conventional procedures. After precipitation of the DNA in 3 volumes of ethanol, the thus isolated plasmid pEL103 DNA is dissolved in 1 ml. of 10 fold diluted TE buffer and is then stored at −20° C.

3. BamHI Digestion of Plasmid pEL103 and Isolation of the Streptomyces Origin of Replication-Containing Fragment About 2 µg. of plasmid pEL103 DNA (prepared in Example 2B) is digested in 1X BamHI buffer (150 mM NaCl, 10 mM Tris pH 8, 10 mM $MgCl_2$) in a total volume of 50 µl. with 16 units (New England Biolab) of BamHI restriction endonuclease. The mixture is incubated at 37° C. for 30 minutes. The DNA is ethanol precipitated according to the method of Example 2A. Next, the DNA is electrophoresed on a 0.5% agarose gel until the desired ~2.9 kb BamHI fragment is separated from other fragments. The isolated ~2.9 kb fragment is removed from the gel, placed in a dialysis bag containing 0.5 ml. Tris-acetate buffer supplemented with 0.5 µg./ml. ethidium bromide and 100 µg./ml. BSA and electroeluted at 50–100V. until the DNA is eluted off the gel. Next, the buffer is removed and the DNA extracted with Sevag. The desired ~2.9 kb BamHI restriction fragment is ethanol precipitated and dissolved in TE buffer for subsequent ligation.

C. Construction of Plasmid pKC326 and *E. coli* K12 BE1041/pKC326

About 2 µg. each of BclI-digested plasmid pKC309 DNA and the ~2.9 kb BamHI Streptomyces origin of replication-containing fragment were ligated in 20 µl. of 1X ligase buffer (50 mM Tris pH 7.8, 10 mM $MgCl_2$, 20 mM DTT, and 1 mM ATP) with 400 units of T4 DNA ligase* overnight at 16° C. The DNA was ethanol precipitated, dried and redissolved in 5 µl. TE for subsequent transformation.

Figure 2:
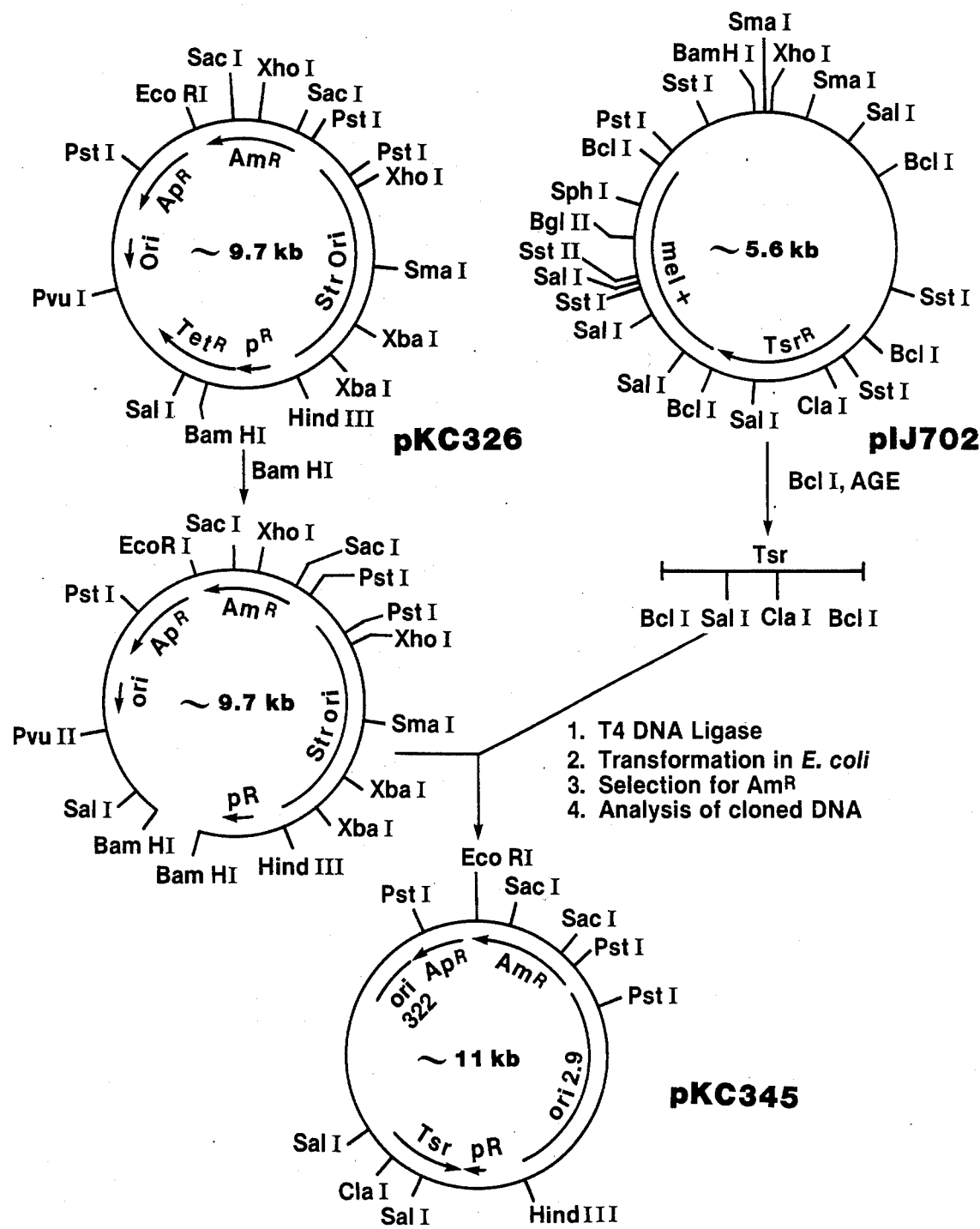
FIG. 2 shows the construction of pKC345.

The resultant plasmid DNA was used to transform *E. coli* K12 BE1041 (NRRL B-15021) according to the procedure of Maniatis et al., 1982, Molecular Cloning, Cold Spring Harbor Laboratory, Cold Spring Harbor, New York. The identity of the desired transformants was conventionally confirmed by screening for the acquisition of a PstI site. The resultant *E. coli* K12 BE1041/pKC326 transformants were conventionally cultured for subsequent production and isolation of plasmid pKC326. A restriction site and functional map of plasmid pKC326 is presented in FIG. 2 of the accompanying drawings.

*T4 DNA ligase can be obtained from the same sources as those identified for restriction enzymes.

D. Final Construction of Plasmid pKC345

1. BamHI Digestion of Plasmid pKC326

About 2 µg. of plasmid pKC326 DNA was digested with BamHI restriction enzyme in substantial accordance with the teaching of Example 2(B)(3), except that the digestion was carried out for 1 hour. The DNA was ethanol precipitated, dried and redissolved in 5 µl. TE buffer for subsequent ligation to a thiostrepton resistance gene isolated from plasmid pIJ702.

2. BclI Digestion of Plasmid pIJ702 and Isolation of the ~b 1 kb Thiostrepton Resistance-Containing Gene About 5 μg. of plasmid pIJ702 DNA (ATCC 39155) is digested with BclI restriction enzyme in substantial accordance with the teaching of Example 2A. The DNA is ethanol precipitated, dried and then dissolved in 5 μl. TE. The DNA is electrophoresed on a 0.5% agarose gel until the desired ~1 kb BclI fragment is separated from other fragments. After staining with ethidium bromide, the desired fragment is located on the gel; Whatman DEAE cellulose paper is placed in a slit prepared ahead of the desired DNA band and the DNA is electrophoresed onto the DEAE paper. The paper is washed with 1 ml. of TE and the DNA is eluted with 400 μl. of TE adjusted to 1M by the addition of an appropriate volume of NaCl. Ihe eluted DNA is ethanol precipitated and finally dissolved in 5 μl. of TE.

3. Ligation and Construction of E. coli K12 BE1041/pKC345

About 2 μg. of BamHI-digested plasmid pKC326 DNA and ~5 μg. of the ~1 kb BclI restriction fragment of plasmid pIJ702 DNA were ligated in substantial accordance with the teaching of Example 2C. After ethanol precipitation, the DNA was further digested with BamHI restriction enzyme to reduce the number of parental plasmids.

The resultant DNA was used to transform E. coli K12 BE1041 according to the procedure of Maniatis et al., 1982. The identity of the desired transformants was conventionally confirmed by screening for ampicillin resistance, tetracycline sensitivity and the acquisition of a SalI site. Competent cells were conventionally cultured for subsequent production and isolation of plasmid pKC345. A restriction site and functional map of plasmid pKC345 is presented in FIG. 2 of the accompanying drawings.

EXAMPLE 3

Construction of pKC354 and E. coli K12 BE1041/pKC354

A. AvaI Digestion of pKC322 and Isolation of the ~2.1 kb AvaI Restriction Fragment About 150 μg. of plasmid pKC322 DNA (NRRL B-15829) was digested in 1X AvaI buffer (60 mM NaCl, 10 mM Tris pH 8, 10 mM DTT and 10 mM MgCl₂) in a total volume of 1 ml. with 15 units (New England Biolabs) of AvaI restriction enzyme for 7 hours at 37° C. Another 20 units of AvaI restriction enzyme was added and the reaction was continued overnight. The resulting DNA in the digestion buffer, was electrophoresed overnight at 50V on a 1% agarose gel in substantial accordance with the teaching of Maniatis et al., 1982.

The ~2.1 kb band was isolated from the gel and the DNA eluted from the gel in substantial accordance with the teaching of Example 2(B)(3). The DNA was extracted twice with phenol and twice with Sevag (chloroform-isoamyl alcohol, 24-1). The ~2.1 kb AvaI fragment was purified using an Elutip-d column (Schleicher and Schuell, Inc., Keene, New Hampshire 03431) and then precipitated with ethanol and redissolved in 20 μl. TE. An equivalent method to purify DNA fragments can also be used whereby the DNA is electrophoresed on a 0.5% agarose gel until the desired fragment is separated from other fragments. Whatman DEAE cellulose paper is then placed in a slit prepared ahead of the desired DNA band and the DNA is electrophoresed onto the DEAE paper. The paper can then be washed with 1 ml. TE and the DNA eluted with 400 μl. TE which is adjusted to 1M by the addition of an appropriate volume of NaCl. The eluted DNA is ethanol precipitated and dissolved in 5 μl. TE for subsequent ligation.

B. SacI Digestion of Plasmid pKC345

About 10 μg. of plasmid pKC345 DNA was digested in 1X SacI buffer (10 mM MgCl₂, 10 mM Tris pH 7.4% and 10 mM DTT) in a total volume of 10 μl. with 5 units (New England Biolabs) of SacI restriction endonuclease for 1 hour at 37° C. The reaction was terminated by increasing the temperature to 70° C. for 5 minutes.

C. Ligation to Construct Plasmid pKC354

About 5 μl. each of the purified ~2.1 kb AvaI restriction fragment and the SacI-digested pKC345 were added to 2 μl. of 10X T4 polymerase buffer (67 mM potassium acetate, 33 mM Tris-acetate pH 7.8, and 10 mM Magnesium acetate). Next, 1 μl. of 20X deoxynucleotides (dATP, dGTP, dCTP, dTTP; final concentration was 10 μM) was added and the volume adjusted to 20 μl. with water. This latter step was performed to make the fragments blunt-ended. After 1 μl. of T4 DNA polymerase was added the mixture was incubated at 37° C. for 5 minutes. This last step was repeated and then 2 μl. of 50 mM EDTA was added and the reaction was terminated by increasing the temperature to 70° C. for 5 minutes. The DNA was extracted once with Sevag and after the volume was increased to 50 μl. with water, the DNA was ethanol precipitated to remove the T4 polymerase salts. The DNA precipitate was suspended in 20 μl. of T4 DNA ligase buffer supplemented with 400 units of T4 DNA ligase (NEB) and the ligation was run at 16° C. for 48 hours.

D. Transformation and Construction of E. coli K12 BE1041/pKC354

Figure 3:
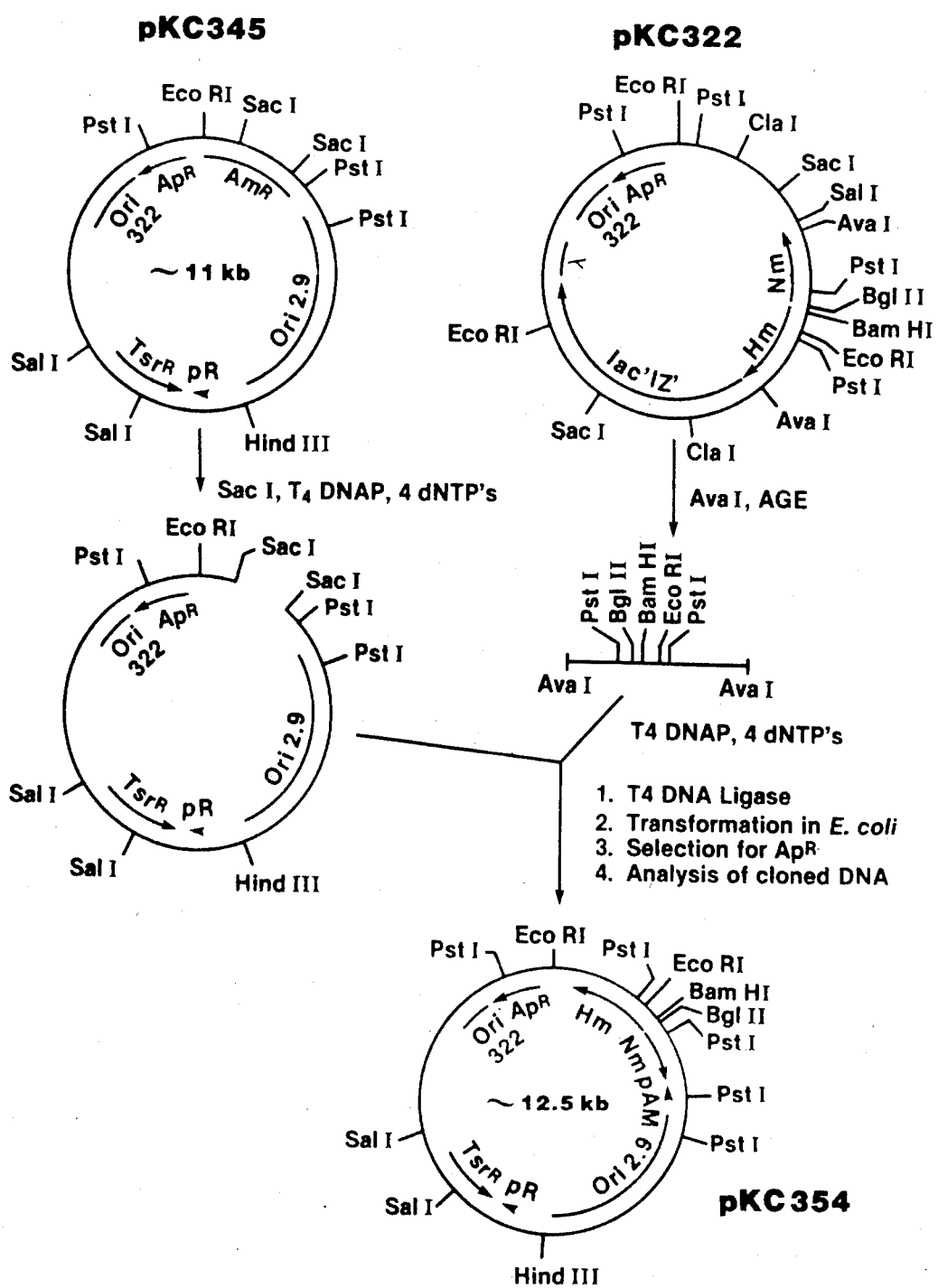
FIG. 3 shows the construction of pKC354.

About 1 μl. of the ligated DNA was used to transform E. coli K12 BE1041 according to the procedure of Maniatis et al., 1982. The transformants were conventionally screened using colony hybridization and a probe prepared by nick translating 2 μl. of the purified ~2.1 kb AvaI restriction fragment. The identity of the transformants was conventionally confirmed by screening for amplicillin resistance and the acquisition of an EcoRI site, a BamHI site and a BglII site. Competent cells were conventionally cultured for subsequent production and isolation of plasmid pKC354. A restriction site and functional map of plasmid pKC354 is presented in FIG. 3 of the accompanying drawings.

EXAMPLE 4

Construction of Plasmid pKC356 and E. coli K12 BE1041/pKC356

A. EcoRI Digestion of Plasmid pKC354

Plasmid pKC356 was constructed by deleting an ~1.5 kb EcoRI fragment from plasmid pKC354. About 10 μg. of pKC354 DNA was digested in 1X EcoRI buffer (100 mM Tris pH 7.5, 50 mM NaCl, and 10 mM MgCl₂) in a total volume of 20 μl. with 24 units (New England Biolabs) of EcoRI restriction enzyme for 1 hour at 37° C. The resulting fragments were isolated by agarose gel electrophoresis and the ~11 kb EcoRI restriction fragment was extracted with phenol and Sevag, purified on an Elutip-d column and ethanol precipitated. The DNA precipitate was redissolved in 10 μl. TE for subsequent ligation.

B. Ligation and Transformation

The resultant DNA was ligated in substantial accordance with the teaching of Example 2C and incubated at 16° C. overnight to promote self-circularization. After incubation, the DNA was ethanol precipitated and redissolved in 10 μl. TE.

About 2 μl. of the resultant DNA was used to transform *E. coli* K12 BE1041 in substantial accordance with the teaching of Maniatis et al., 1980. The identity of the desired transformants was conventionally confirmed by screening for ampicillin resistance and for the deletion of an EcoRI restriction site. Competent cells were conventionally cultured for subsequent production and isolation of plasmid pKC356. A restriction site and functional map of plasmid pKC356 is presented in FIG. 4 of the accompanying drawings.

EXAMPLE 5

Construction of Plasmid pKC417

A. XhoII Digestion of Plasmid pKC283

About 5.4 μg. of plasmid pKC283 DNA (NRRL B-15830) was digested in 1X XhoII buffer (10 mM Tris pH 7.5, 10 mM MgCl$_2$, 10 mM DTT, 0.01% Triton X-100) in a total volume of 20 μl. with 5.6 units (New England Biolab) of XhoII restriction endonuclease. The mixture was incubated at 37° C. for 1½ hours and then the reaction was terminated by increasing the temperature to 70° C. for 5 minutes. This XhoII digestion generates fragments with complimentary XhoII or BglII ends. The DNA was ethanol precipitated and further digested with two different restriction enzymes to cut the DNA into many fragments. These digestions do not, however, affect the integrity of the particular ~137 bp BglII fragment containing the λp$_L$ promoter sequence. Thus, the pKC283 DNA was next digested with 10 units of PvuII restriction endonuclease in buffer (60 mM NaCl, 10 mM Tris pH 7.5, 10 mM MgCl$_2$ and 10 mM DTT) for 1½ hours at 37° C. and then digested with 10 units of SmaI restriction endonuclease in buffer (20 mM KCl, 10 mM Tris pH 8.0, 10 mM MgCl$_2$ and 10 mM DTT) for 1 hour at 37° C. After ethanol precipitation, the DNA was dissolved in 5 μl. TE for subsequent ligation.

B. BglII Digestion of Plasmid pKC356

The desired digestion was performed in substantial accordance with the teaching of Example 2(B)(3) except that BglII restriction enzyme and buffer (60 mM NaCl, 10 mM Tris pH 7.4, 10 mM MgCl$_2$ and 10 mM DTT) were used in place of BamHI restriction enzyme and buffer. Additionally, plasmid pKC356 was used in place of plasmid pEL103. The DNA was ethanol precipitated and then redissolved in 10 μl. TE.

C. Ligation and Construction of *E. coli* K12 B1315/pKC417

Any *Escherichia coli* strain containing the λ cI857 gene would serve as a suitable recipient for this experiment. Such strains include, for example, K12ΔH1Δtrp (Castellazzi et al., 1972, Mol. Gen. Genet. 117:211; Bernard et al., 1979, Gene 5:59). The desired ligation and subsequent transformation of *E. coli* K12 BE1315 was performed in substantial accordance with the teaching of Example 2C except that the cells were not heat shocked. The ligation succeeded in producing recombinant plasmids wherein the ~137 bp BglII-digested fragment of plasmid pKC283 was inserted at the unique BglII site directly upstream from the promoterless neomycin phosphotransferase gene. The identity of the desired transformants was conventionally confirmed by screening for neomycin resistance and ampicillin resistance. Additionally, the cells were screened for the acquisition of an additional BglII site. The resultant transformants were conventionally cultured for subsequent production and isolation of plasmid pKC417. A restriction site and functional map of plasmid pKC417 is presented in FIG. 4 of the accompanying drawings.

EXAMPLE 6

Construction of *Streptomyces ambofaciens*/pKC356 and *S. ambofaciens*/pKC417

About 1 μg. each of the DNA from Examples 4 and 5 and 200 μl. of protoplasts of *Streptomyces ambofaciens*, a strain deposited and made part of the permanent stock culture collection of the Northern Regional Research Laboratories, Peoria, Ill., from which it is available to the public under the accession number NRRL 2420, were mixed gently with 500 μl. of 55% polyethylene glycol (Sigma) in P medium (Hopwood and Wright, 1978, Molecular and General Genetics 162:307), and then aliquots of 25 μl. and 250 μl. were plated onto R2YE* plates with 3 ml. of R2YE top agar. The plates were incubated for 18 hours at 30° C. and then overlayed with 3 ml. of R2YE top agar containing sufficient neomycin and thiostrepton** for a final concentration of 10 μg./ml. and 25 μg./ml. respectively. The plates were then incubated for an additional 3 days at 30° C. The resultant *S. ambofaciens*/pKC356 thiostrepton resistant colonies and *S. ambofaciens*/pKC417 neomycin and thiostrepton resistant colonies were isolated according to known procedures, cultured, and then the plasmid structures wer conventionally identified by restriction enzyme and agarose gel electrophoretic analysis (Maniatis et al., 1982).

*R2YE medium was prepared, with the following composition per liter: Sucrose-103 g. 2.5% K$_2$SO$_4$-10 ml. MgCl$_2$-10.1 g. Glucose-10 g. Casamino acids-0.1 g. Agar-22 g. Trace Element Mix-2 ml. 0.5% KH$_2$PO$_4$-10 ml. 1M CaCl$_2$-20 ml. Proline-3 g. 0.25M TES pH 7.2-100 ml. 10% Yeast extract-50 ml.
**Antibiotic neomycin can be obtained from Sigma, St. Louis, Mo.

Antibiotic thiostrepton can be obtained from E. R. Squibb and Sons, Inc., Princeton, N.J. 08540.

EXAMPLE 7

Expression of Neomycin Phosphotransferase Activity in *Streptomyces ambofaciens*

The transformed Streptomyces cultures carrying plasmids pKC356 and pKC417, respectively, were grown overnight in 250 ml. of Tryptic Soy broth supplemented with 25 μg./ml. of the antibiotic thiostrepton. The cells were collected by centrifugation (10,000 rpm, 10 minutes) and the pellet washed with 100 ml. of 10 mM Tris pH 8.0. After another cycle of centrifugation followed by a wash, the centrifugation was repeated and the cell pellet was resuspended in 5 ml. of a solution containing 10 mM Tris pH 8.0, 0.5 mM MgCl$_2$, 0.1 mM EDTA and 1 mM DTT. The cells were disrupted by sonication which was followed by centrifugation in a SS34 rotor (16,000 rpm, 30 minutes, 4° C.). The supernatant was removed and DNAse was added to a final concentration of 4 μg./ml. This solution was centrifuged in a 75 Ti rotor (45,000 rpm, 2 hours, 4° C.) and the supernatant was removed. After the protein concentration was determined, about 40 μg. of protein was added to 50 μl. of phosphotransferase assay reaction mix*, vortexed and then incubated at 30° C. for 15 minutes. Next, approximately 25 μl. of the solution was pipetted onto Whatman P-81 filters and placed for 5 minutes in an ~80° C. water bath. After the filters were washed and dried, the amount of phosphotransferase activity was determined. The results are indicated in Table 1. The *E. coli* extracts were prepared in the same manner and are included in the table.

*Phosphotransferase assay reaction mix was prepared with the following composition: 4 mM Neomycin, 13 mM Tris pH 8.0, 8.4 mM MgCl$_2$, 80 mM NH$_4$Cl, 2 mM DTT, 2 mM ATP (contains [γ-$^{32}$P]-ATP so the final specific activity is 9-10 μCi/μmole).

TABLE 1

Expression of Neomycin Phosphotransferase Activity in *Escherichia coli* and *Streptomyces ambofaciens*

| Transformant | Phenotype[a] | Enzymatic activity[b] |
|---|---|---|
| 1. *S. ambofaciens*/pKC356 | S | 373 cpm |
| 2. *S. ambofaciens*/pKC417 | R | 38,000 cpm |
| 3. Control | | 68 cpm |
| 4. *E. coli* K12 BE1041/pKC356 | S | 1267 cpm |
| 5. *E. coli* K12 BE1315/pKC417[c] | R | 26,839 cpm |
| 6. *E. coli* K12 BE1315/pKC417[d] | R | 207,634 cpm |

Legend
[a]The phenotype of *E. coli* cells were scored on tryptone yeast extract plates (Rao and Rogers, 1979, Gene 7:79-82) supplemented with neomycin at 25 μg./ml. The phenotype of *S. ambofaciens* cells was scored on trypticase soy agar plates (Kuhstoss and Rao, 1983, Gene 26:295-299) supplemented with neomycin at 1 μg./ml. S, Sensitive; R, resistant.
[b]Enzymatic activity represents counts per minute (Cerenkov radiation) for 25 μl. of reaction mixture.
[c]Cells were grown continuously at 42° C. where λ cI repressor was inactivated.
[d]Cells were grown at 30° C. and derepressed for 5 hours at 42° C.

We claim:

1. A method of using bacteriophage lambda $p_L$ promoter to produce a functional polypeptide in Streptomyces, said method comprising:
   (a) transforming a Streptomyces host cell with a selectable and autonomously replicating recombinant DNA expression vector comprising:
      (1) the bacteriophage $\lambda p_L$ promoter-operator transcriptional activating sequence;
      (2) a translational activating sequence;
      (3) a DNA sequence that codes for a functional polypeptide; and
   (b) culturing said transformed cell under conditions suitable for expression of said polypeptide,
subject to the limitation that said expression vector sequentially contains said $\lambda p_L$ promoter-operator transcriptional activating sequence, said translational activating sequence and said DNA sequence that codes for a functional polypeptide such that a translatable mRNA transcript encodes the functional polypeptide.

2. The method of claim 1 wherein the expression vector is a plasmid.

3. The method of claim 1 wherein the expression vector is plasmid pKC417.

4. The method of claim 1 in which the transformed Streptomyces host cell is selected from the group consisting of *Streptomyces ambofaciens, Streptomyces aureofaciens, Streptomyces cinnamonesis, Streptomyces fradiae, Streptomyces qranuloruber, Streptomyces qriseofuscus,* and *Streptomyces lividans.*

5. The method of claim 4 in which the transformed Streptomyces host cell is *Streptomyces ambofaciens.*

6. The method of claim 4 in which the transformed Streptomyces host cell is *Streptomyces fradiae.*

7. The method of claim 4 in which the transformed Streptomyces host cell is *Streptomyces lividans.*

8. The method of claim 1 wherein the gene that encodes a functional polypeptide is selected from the group consisting of genes that encode neomycin phosphotransferase, human pre-proinsulin, human proinsulin, human insulin A-chain, human insulin B-chain, non-human insulin, human growth hormone, non-human growth hormone, bovine growth hormone, porcine growth hormone, human interferon, non-human interferon, viral antigen, urokinase, any peptide hormone and any polypeptide enzyme.

9. The method of claim 8 wherein the DNA sequence that codes for a functional polypeptide is neomycin phosphotransferase.

10. The method of claim 1 wherein the bacteriophage $\lambda p_L$ promoter-operator transcriptional activating sequence is derived from plasmid pKC283.

11. A plasmid selected from the group consisting of pKC309, pKC322, pKC283, pKC354, and pKC356.

12. The plasmid of claim 11 which is pKC283.

13. A Streptomyces host cell transformed by a recombinant DNA expression vector capable of selection and autonomous replication in said Streptomyces host cell, said vector comprising:
   (a) the bacteriophage $\lambda P_L$ promoter-operator transcription activating sequence;
   (b) a translational activating sequence; and
   (c) a DNA sequence that codes for a functional polypetide,
subject to the limitation that said expression vector sequentially contains said $\lambda P_L$ promoter-operator transcriptional activating sequence, said translational activating sequence, and said DNA sequence that codes for a functional polypeptide such that a translatable mRNA transscript encodes said functional polypeptide.

14. The transformed Streptomyces host cell of claim 13 which is *Streptomyces ambofaciens*/pKC417.

15. A selectable recombinant DNA expression vector which replicates in Streptomyces which comprises:
   (a) the bacteriophage $\lambda P_L$ promoter-operator transcriptional activating sequence;
   (b) a translational activating sequence; and
   (c) a DNA sequence that codes for a functional polypeptide,
subject to the limitation that in a Streptomyces host cell said expression vector sequentially contais said $\lambda P_L$ promoter-operater transcriptional activating sequence, said translational activating sequence, and said DNA sequence that codes for a functional polypeptide such that a translatable mRNA transcript encodes said functional polypeptide.

16. The vector of claim 15 which is a plasmid.

17. The plasmid of claim 16 which is pKC417.

* * * * *